US010802031B2

(12) United States Patent
Abe et al.

(10) Patent No.: US 10,802,031 B2
(45) Date of Patent: Oct. 13, 2020

(54) MARKER FOR DETERMINING DIABETIC NEPHROPATHY

(71) Applicant: TOHOKU UNIVERSITY, Miyagi (JP)

(72) Inventors: Takaaki Abe, Miyagi (JP); Susumu Ogawa, Miyagi (JP); Yoshihisa Tomioka, Miyagi (JP)

(73) Assignee: TOHOKU UNIVERSITY, Miyagi (JP)

( * ) Notice: Subject to any disclaimer, the term of this patent is extended or adjusted under 35 U.S.C. 154(b) by 320 days.

(21) Appl. No.: 15/763,242

(22) PCT Filed: Sep. 29, 2016

(86) PCT No.: PCT/JP2016/004394
§ 371 (c)(1),
(2) Date: Jul. 17, 2018

(87) PCT Pub. No.: WO2017/056498
PCT Pub. Date: Apr. 6, 2017

(65) Prior Publication Data
US 2018/0313851 A1 Nov. 1, 2018

(30) Foreign Application Priority Data

Sep. 30, 2015 (JP) ................. 2015-193638

(51) Int. Cl.
*G01N 33/84* (2006.01)
*G01N 33/53* (2006.01)
*G01N 33/68* (2006.01)

(52) U.S. Cl.
CPC ..... *G01N 33/6893* (2013.01); *G01N 33/5308* (2013.01); *G01N 33/84* (2013.01); *G01N 33/53* (2013.01); *G01N 2800/347* (2013.01); *G01N 2800/56* (2013.01)

(58) Field of Classification Search
CPC ............... G01N 33/6893; G01N 33/84; G01N 33/5308; G01N 2800/347; G01N 2800/56; G01N 33/53
See application file for complete search history.

(56) References Cited

FOREIGN PATENT DOCUMENTS

| JP | 2012-237623 | 12/2012 |
| JP | 2014-032046 | 2/2014 |
| WO | 2013/048344 | 4/2013 |
| WO | 2013/188333 | 12/2013 |

OTHER PUBLICATIONS

Niewczas, Monika A. et al., "Uremic solutes and risk of end-stage renal disease in type 2 diabetes: metabolomic study," International Society of Nephrology, Iss. 5, vol. 85, p. 1214-1224, DOI: 10.1038/ki.2013.497 (Year: 2014).*

Niewczas, Monica A., et al., "Uremic solutes and risk of end-stage renal disease in type 2 diabetes: metabolomic study," Jan. 15, 2014, Kidney International Journal, Ed. 85, Iss. 5, p. 1214-1224, DOI: 10.1038/ki.2013.497. (Year: 2014).*
Dihazi et al, Characterization of diabetic nephropathy by urinary proteomic analysis: identification of a processed ubiquitin form as a differentially excreted protein in diabetic nephropathy patients, Clin Chem 2007, 53:1636-1645.
Kikuchi, Metabolomic search for uremic toxins as indicators of the effect of an oral sorbent AST-120 by liquid chromatography/tandem mass spectrometry, J Chromatogr B, 2010, vol. 878 No. 29, p. 2997-3002.
Hirata, "Indoxyl Sulfate Oyobi sonota no Nyodokusho Busshitsu no Hinketsu Yuhatsu Sayo ni Kanasuru Hikaku Kento", The Japanese Journal of Nephrology, 2013, vol. 55, No. 3, p. 428, P-490, Partial Translation.
Kobayashi, Exploration of novel predictive markers in rat plasma of the early stages of chronic renal failure, Anal Bioanal Chem, 2014, vol. 406 No. 5, p. 1365-1376, Abstract, Fig. 3 (F).
Mischak, et al, Proteomic analysis for the assessment of diabetic renal damage in humans, Clin Sci (Lond) Nov. 1, 2004, 107:485-495, Abstract only.
Ng, A metabolomic stufy of low estimated GFR in non-proteinuric type 2 diabetes mellitus, Diabetologia, 2012, vol. 55 No. 2, p. 499-508, Abstract, Methods (Metabolomic data preprocessing), p. 503.
Niwa, "Analysis of Phenols in Uremic Serum by Gas Chromatography-mass Spectrometry", The Japanese Journal of Nephrology, 1981, vol. 23, No. 6, pp. 777 to 788, p. 782, Partial Translation.
Notification of Transmittal of Copies of Translation of the International Preliminary Report on Patentability and the Translation of the International Preliminary Report on Patentability issued by The International Bureau of WIPO on Apr. 5, 2018 for International Application No. PCT/JP2016/004394, 7 pages.
Ogawa, "Tonyobyosei Jinsho no Shinko ni Okeru Kecchu Oyobi Nyochu osteopontin to Igi", Folia endocrinologica Joponica, Apr. 1, 2015 (Apr. 1, 2015), vol. 91, No. 1, p. 320, P1-10-1.
Ogawa, "Tonyobyosei Jinsho no Byoki Shinko to Ensho Marker no Zodai Oyobi Shinkekkan Shogai Shinko no Kento", Diabetes Front, 2006, vol. 17, No. 5, p. 671.
Sakamoto, "Tonyobyo Jinsho ni Okeru Kecchu CyclophilinA no Shinki Biomarker to shite no Yuyosei ni Tsuite", The Journal of the Japan Diabetic Society, 2013, vol. 56, No. Supplement 1, p. S.365, III-8-20.

(Continued)

*Primary Examiner* — Jennifer Wecker
*Assistant Examiner* — Michael Paul Shimek
(74) *Attorney, Agent, or Firm* — Occhiuti & Rohlicek LLP

(57) ABSTRACT

An object of the present invention is to provide a biomarker capable of determining the onset risk or the stage of diabetic nephropathy (early-stage diabetic nephropathy in particular). Diabetic nephropathy is determined by measuring or quantitatively determining a concentration of phenyl sulfate or a salt thereof (a phenyl sulfate) contained in a biological sample, preferably plasma or urine, collected from a test subject to detect a phenyl sulfate. The present invention exhibits excellent effects particularly for stage determination for stage 1 (pre-nephropathy stage) to stage 3 (overt nephropathy stage), or for determination of onset risk of diabetic nephropathy (diabetic nephropathy at pre-nephropathy stage).

4 Claims, No Drawings

(56) References Cited

OTHER PUBLICATIONS

Niewczas et al. "Uremic Solutes and Risk of End Stage Renal Disease in Type 2 Diabetes" *Kidney Int.*, 85: 1214-1224, Jan. 2014.

Niewczas, et al. "Uremic Solutes and Rise of End Stage Renal Disease in Type 2 Diabetes" *Kidney Int.*, 85(5): 1214-1224, May 2014.

Stec et al., "Alterations of Urinary Metaolite Profile in Model Diabetic Nephropathy," *Biochemical and Biophysical Research Communications*, 456: 610-614 (2015).

Yoshiharu Itoh et al, Protein-Bound Uremic Toxins in Hemodialysis Patients Measured by Liquid Chromatography/Tandem Mass Spectrometry and Their Effects on Endothelial ROS Production. Anal Bioanal Chem, 2012, vol. 403, pp. 1841-1850.

\* cited by examiner

MARKER FOR DETERMINING DIABETIC NEPHROPATHY

CROSS REFERENCE TO RELATED APPLICATIONS

This application is a National Phase under 35 USC 371 of International Application No. PCT/JP2016/004394 filed on Sep. 29, 2016, which claims priority to Japanese Application No. 2015-193638 filed Sep. 30, 2015 the contents of which are hereby incorporated by reference in their entirety.

TECHNICAL FIELD

The present invention relates to a method for determining diabetic nephropathy, and a biomarker for determining diabetic nephropathy to be used in the method for determining diabetic nephropathy.

BACKGROUND ART

It is known that diabetes causes various chronic vascular complications, and the prognosis of the disease is varied by the complications. Among the complications, diabetic nephropathy is significant for life prognosis, and it is desired to diagnose the onset and the onset risk at an early stage for inhibiting progression.

Conventionally, the stage of diabetic nephropathy has been diagnosed on the basis of not only history of diabetes but also change in urinary findings (detection of proteinuria/microalbuminuria), degradation in estimated glomerular filtration rate (eGFR), and ophthalmological findings (observation of fundus blood vessel lesion). It has been regarded, however, that such diagnoses are disadvantageously insufficient for distinction from other kidney diseases except for diabetic nephropathy.

On the other hand, novel urinary or blood biomarkers have been searched for and studied in recent years. For example, a urinary protein useful for identifying a diabetic nephropathy patient among type 2 diabetes patients by using an SELDI (Surface Enhanced Laser Desorption/Ionization) time-of-flight mass spectrometer has been reported (non-patent document 1). Besides, a pattern that can be used for distinguishing a type 2 diabetes patient from a healthy individual by profiling a urinary polypeptide using a capillary electrophoresis-mass spectrometer (CE-MS) has been found (non-patent document 2). The inventions described in these documents do not, however, relate to a biomarker capable of determining the stage of diabetic nephropathy or the onset risk of diabetic nephropathy. Furthermore, it is reported that a biomarker capable of early recognition of diabetic nephropathy using CE-TOFMS has been identified (patent document 1). Although it is described that there is a statistically significant difference in the concentration of the identified biomarker (compound) between different stages, the difference is so small that it is unknown whether or not it can be practically used. Besides, this biomarker cannot determine the onset risk of diabetic nephropathy.

PRIOR ART DOCUMENTS

Patent Documents

Patent Document 1: Japanese unexamined Patent Application Publication No. 2014-32046

Non-Patent Documents

Non-patent Document 1: Dihazi, H. et al., Clin Chemi 2007, 53: 1636-1645

Non-patent Document 2: Mischak, H. et al., Clin Sci (Lond) 2004, 107: 485-495

SUMMARY OF THE INVENTION

Object to be Solved by the Invention

An object of the present invention is to provide a biomarker capable of determining the onset risk or the stage of diabetic nephropathy (early-stage diabetic nephropathy in particular).

Means to Solve the Object

In order to solve the above-described object, the present inventors have analyzed the relationship between a phenyl sulfate salt (PS) concentration and ACR, that is, an index of diabetic nephropathy, and have found that the onset risk and the stage of diabetic nephropathy (early-stage diabetic nephropathy in particular) can be determined by using increase of the PS concentration as an indicator, resulting in accomplishing the present invention.

Specifically, the present invention provides:

[1] A method for determining diabetic nephropathy, comprising detecting phenyl sulfate or salt thereof contained in a biological sample collected from a test subject.

[2] The method for determining diabetic nephropathy according to [1], wherein the biological sample is blood or urine.

[3] The method for determining diabetic nephropathy according to [2], wherein the test subject is a test subject who has not developed diabetic nephropathy, and when a concentration of the phenyl sulfate or salt thereof contained in blood collected from the test subject is not less than a prescribed threshold value, it is indicative that the test subject has a high possibility of developing diabetic nephropathy.

[4] The method for determining diabetic nephropathy according to [3], wherein the prescribed threshold value is 5.5 (nmol/mL).

[5] The method for determining diabetic nephropathy according to [2], wherein the test subject is a test subject who is unknown to have diabetic nephropathy or not, or a test subject whose stage of diabetic nephropathy is unknown, and when a concentration of the phenyl sulfate or salt thereof contained in blood collected from the test subject is less than a prescribed threshold value, it is indicative that the test subject has a high possibility of being classified as diabetic nephropathy at pre-nephropathy stage, when a concentration of the phenyl sulfate or salt thereof contained in blood collected from the test subject falls in a range of prescribed values A, it is indicative that the test subject has a high possibility of being classified as diabetic nephropathy at early nephropathy stage or overt nephropathy stage, and when a concentration of the phenyl sulfate or salt thereof contained in blood collected from the test subject falls in a range of prescribed values B, it is indicative that the test subject has a high possibility of being classified as diabetic nephropathy at overt nephropathy stage.

[6] The method for determining diabetic nephropathy according to [5], wherein the prescribed threshold value is 0.51 (nmol/mL), the prescribed values A are over 54.4 (nmol/mL) to 159 (nmol/mL), and the prescribed values B are over 74.1 (nmol/mL) to 159 (nmol/mL).

[7] A biomarker for determining diabetic nephropathy, comprising phenyl sulfate or salt thereof.

[8] The biomarker according to [7], wherein determination of diabetic nephropathy is determination of onset risk of diabetic nephropathy.

[9] The biomarker according to [7], wherein determination of diabetic nephropathy is determination of stage of diabetic nephropathy.

The determination method of the present invention is a method for assisting diagnosis of diabetic nephropathy made by a doctor, and does not include a diagnostic action carried out by the doctor. Besides, as another aspect of the determination method, a method for collecting data to be used for diagnosis of diabetic nephropathy can be provided.

Furthermore, another embodiment of the present invention provides a method for diagnosing diabetic nephropathy including detecting phenyl sulfate or salt thereof contained in a biological sample collected from a test subject. The diagnosis method preferably further includes a step of treating the test subject (patient) diagnosed with diabetic nephropathy for improving the renal function of the diagnosed test subject (patient).

Besides, as another embodiment of the present invention, phenyl sulfate or salt thereof to be used as a biomarker in a method for diagnosing (determining) diabetic nephropathy can be provided.

Effect of the Invention

According to the present invention, the onset risk or the onset of diabetic nephropathy at a comparatively early stage can be accurately determined, and therefore, the number of medical examinees for diabetic nephropathy in periodic medical examination necessary for early detection of diabetic nephropathy can be expected to increase, and in addition, it is possible to prevent the onset of diabetic nephropathy or to effectively treat diabetic nephropathy at an early stage, and thus, effects to improve QOL (Quality of Life) and to reduce medical expense can be expected by preventing progression to renal dysfunction or renal failure.

MODE OF CARRYING OUT THE INVENTION

A method for determining diabetic nephropathy of the present invention (hereinafter simply referred to as the "present determination method") is not especially limited as long as it is a method for determining diabetic nephropathy comprising measuring or quantitatively determining a concentration of phenyl sulfate or salt thereof (hereinafter sometimes generically referred to as a phenyl sulfate) contained in a biological sample collected from a test subject (a donor) for detecting a phenyl sulfate (excluding a diagnostic action carried out by a doctor), and a biomarker for determining diabetic nephropathy of the present invention (hereinafter simply referred to as the "present biomarker") is not especially limited as long as it is a biomarker, containing a phenyl sulfate, for determining (diagnosing) diabetic nephropathy in a test subject, and here, the "determination of diabetic nephropathy" includes determination of the onset risk of diabetic nephropathy and determination of the stage of diabetic nephropathy.

The stage of diabetic nephropathy can be classified on the basis of a urinary albumin/creatinine ratio (ACR) corresponding to an index of early diabetic nephropathy, or an estimated glomerular filtration rate (eGFR). For example, in employing classification based on diabetic nephropathy stage classification revised by Joint Committee on Diabetic Nephropathy in December 2013, a diabetes patient showing ACR less than 30 (mg/g) corresponding to normal albuminuria and eGFR of not less than 30 (mL/min/1.73 $m^2$) is classified as stage 1 (pre-nephropathy stage), a diabetes patient showing ACR of 30 to 299 (mg/g) corresponding to microalbuminuria and eGFR of not less than 30 (mL/min/1.73 $m^2$) is classified as stage 2 (early nephropathy stage), a diabetes patient showing ACR of not less than 300 (mg/g) corresponding to overt albuminuria or persistent proteinuria of not less than 0.5, and eGFR of not less than 30 (mL/min/1.73 $m^2$) is classified as stage 3 (overt nephropathy stage), a diabetes patient showing eGFR of less than 30 (mL/min/1.73 $m^2$) (preferably, a diabetes patient showing ACR of not less than 300 [mg/g] corresponding to overt albuminuria, or persistent proteinuria of not less than 0.5) is classified as stage 4 (renal failure stage), and a diabetes patient on dialysis treatment is classified as stage 4 (dialysis therapy stage). The present determination method and the present biomarker exhibit excellent effects particularly for making stage determination for stage 1 (pre-nephropathy stage) to stage 3 (overt nephropathy stage).

In the present invention, the term "onset of diabetic nephropathy" means a state where diabetic nephropathy at stage 2 (early nephropathy stage) or later where microalbuminuria is detected has developed. In other words, stage 1 (pre-nephropathy stage) corresponds to a preclinical state of diabetic nephropathy, and stage (early nephropathy stage) corresponds to a state after the onset of diabetic nephropathy (a state where diabetic nephropathy has developed). The present determination method and the present biomarker exhibit excellent effects particularly for determination of the onset risk of diabetic nephropathy (diabetic nephropathy at early nephropathy stage) at stage 1 (pre-nephropathy stage).

Examples of the test subject include a test subject who has not developed diabetic nephropathy, a test subject who is unknown to have diabetic nephropathy or not, and a test subject (a diabetic nephropathy patient) whose stage (progression stage) of diabetic nephropathy is unknown. The test subject who is unknown to have diabetic nephropathy or not includes a test subject who has been previously affected by diabetic nephropathy but is unknown to have diabetic nephropathy or not at the time of examination, and the diabetic nephropathy patient whose stage (progression stage) of diabetic nephropathy is unknown includes a diabetic nephropathy patient that has been previously affected by diabetic nephropathy but whose stage (progression stage) of diabetic nephropathy at the time of examination is unknown.

Examples of the biological sample include a non-liquid sample such as a tissue, a cell or an organ, and a liquid sample such as blood, urine or saliva, and among these, blood (plasma or serum) or urine is preferred.

In the present determination method, phenyl sulfate to be detected or phenyl sulfate contained in the present biomarker is the following compound (molecular weight 174.17).

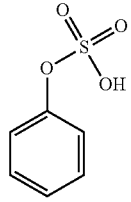 [SMILES: O=S(=O)(O)Oc1ccccc1]

In the present determination method, a phenyl sulfate salt to be detected or a phenyl sulfate salt contained in the present biomarker includes a metal salt generated from aluminum, calcium, lithium, magnesium, potassium, sodium or zinc, or an organic salt generated from N,N'-dibenzylethylenediamine, chloroprocaine, choline, diethanolamine, ethylenediamine, N-methylglucamine, lysine or procaine.

In the present determination method, when a concentration of a phenyl sulfate contained in a biological sample collected from a test subject who has not developed diabetic nephropathy is higher than that in a biological sample derived from a healthy individual, it is indicative that the test subject has a high possibility (risk) of developing diabetic nephropathy, and when a concentration of a phenyl sulfate contained in a biological sample collected from a test subject who has not developed diabetic nephropathy is not higher than that in a biological sample derived from a healthy individual, it is indicative that the test subject has a low possibility (risk) of developing diabetic nephropathy. Incidentally, the biological sample derived from the healthy individual is preferably subjected, after collection, to a similar treatment as the biological sample derived from the test subject.

Besides, in the present determination method, when a concentration of a phenyl sulfate contained in a biological sample collected from a test subject who is unknown to have diabetic nephropathy or not or a test subject whose stage of diabetic nephropathy is unknown is higher than that in a biological sample derived from a control, it is indicative that the test subject has a high possibility of having diabetic nephropathy at advanced stage as compared with the control, and when a concentration of a phenyl sulfate contained in a biological sample collected from a test subject who is unknown to have diabetic nephropathy or not or a test subject whose stage of diabetic nephropathy is unknown is not higher than that in a biological sample derived from a control, it is indicative that the test subject has a low possibility of having diabetic nephropathy at advanced stage as compared with the control. Incidentally, the biological sample derived from the control is preferably subjected, after collection, to a similar treatment as the biological sample derived from the subject.

Besides, in the present determination method, when a concentration of a phenyl sulfate contained in blood collected from a test subject who has not developed diabetic nephropathy is not less than (over) a prescribed threshold value, for example, not less than 5.2 (nmol/mL), preferably not less than 5.5 (nmol/mL), more preferably not less than 6.5 (nmol/mL), and further preferably not less than 7.5 (nmol/mL), it is indicative that the test subject has a high possibility of developing diabetic nephropathy, and when a concentration of a phenyl sulfate contained in blood collected from a test subject who has not developed diabetic nephropathy is less than (not more than) a prescribed threshold value, for example, less than 5.2 (nmol/mL), preferably less than 5.5 (nmol/mL), more preferably less than 6.5 (nmol/mL), and further preferably less than 7.5 (nmol/mL), it is indicative that the test subject has a low possibility of developing diabetic nephropathy.

Furthermore, in the present determination method, when a concentration of a phenyl sulfate contained in blood collected from a test subject who is unknown to have diabetic nephropathy or not or a test subject whose stage of diabetic nephropathy is unknown is less than (not more than) a prescribed threshold value, for example, less than 0.51 (nmol/mL), preferably not more than 0.50 (nmol/mL), more preferably not more than 0.49 (nmol/mL), further preferably not more than 0.48 (nmol/mL), and still more preferably not more than 0.47 (nmol/mL), it is indicative that the test subject has a high possibility of being classified as diabetic nephropathy at stage 1 (pre-nephropathy stage), and when it is not less than (over) a prescribed threshold value, for example, not less than 0.51 (nmol/mL), preferably over 0.50 (nmol/mL), more preferably over 0.49 (nmol/mL), further preferably over 0.48 (nmol/mL), and still more preferably over 0.47 (nmol/mL), it is indicative that the test subject has a low possibility of being classified as diabetic nephropathy at stage 1 (pre-nephropathy stage).

Besides, in the present determination method, when a concentration of a phenyl sulfate contained in blood collected from a test subject who is unknown to have diabetic nephropathy or not, or from a test subject whose stage of diabetic nephropathy is unknown is over (not less than) a prescribed threshold value, for example, over 54.4 (nmol/mL), preferably not less than 54.5 (nmol/mL), more preferably not less than 54.6 (nmol/mL), and further preferably not less than 54.7 (nmol/mL), still more preferably in a range of prescribed values, for example, a range of over 54.4 (nmol/mL) to 159 (nmol/mL), particularly preferably a range of 54.5 (nmol/mL) to 159 (nmol/mL), and most preferably a range of 54.6 (nmol/mL) to 159 (nmol/mL), it is indicative that the test subject has a high possibility of being classified as diabetic nephropathy at stage 2 (early nephropathy stage) or stage (overt nephropathy stage). Further, when a concentration of a phenyl sulfate contained in blood collected from a test subject who is unknown to have diabetic nephropathy or not, or from a test subject whose stage of diabetic nephropathy is unknown is not more than (less than) or not less than (over) a prescribed threshold value, for example, not more than 54.4 (nmol/mL) or not less than 159 (nmol/mL), preferably less than 54.5 (nmol/mL) or not less than 159 (nmol/mL), more preferably less than 54.6 (nmol/mL) or not less than 159 (nmol/mL), and further preferably less than 54.7 (nmol/mL) or not less than 159 (nmol/mL), it is indicative that the test subject has a high possibility of being classified as diabetic nephropathy at stage 2 (early nephropathy stage) or stage 3 (overt nephropathy stage).

Besides, in the present determination method, when a concentration of a phenyl sulfate contained in blood collected from a test subject who is unknown to have diabetic nephropathy or not, or from a test subject whose stage of diabetic nephropathy is unknown is over (not less than) a prescribed threshold value, for example, over 74.1 (nmol/mL), preferably not less than 74.2 (nmol/mL), more preferably not less than 74.3 (nmol/mL), further preferably not less than 74.4 (nmol/mL), and still more preferably in a range of prescribed values, for example, a range of over 74.1 (nmol/mL) to 159 (nmol/mL), particularly preferably a range of 74.2 (nmol/mL) to 159 (nmol/mL), and most preferably a range of 74.3 (nmol/mL) to 159 (nmol/mL), it is indicative that the test subject has a high possibility of being classified as diabetic nephropathy at stage 3 (overt nephropathy stage). Further, when a concentration of a phenyl sulfate contained in blood collected from a test subject who is unknown to have diabetic nephropathy or not, or from a test subject whose stage of diabetic nephropathy is unknown is not more than (less than) or over (not less than) a prescribed threshold value, for example, not more than 74.1 (nmol/mL) or over 159 (nmol/mL), preferably not more than 74.2 (nmol/mL) or over 159 (nmol/mL), more preferably not more than 74.3 (nmol/mL) or over 159 (nmol/mL), and further preferably not more than 74.4 (nmol/mL) or over 159 (nmol/mL), it is regarded that the test subject has a low possibility of being classified as diabetic nephropathy at stage 3 (overt nephropathy stage).

The prescribed threshold values (cut-off values) or the prescribed values can be calculated by a usual method based on data of concentrations of a phenyl sulfate in biological samples collected from diabetic nephropathy patients, healthy individuals and/or controls.

In the present determination method, a method for detecting a phenyl sulfate can be any method as long as a concentration of a phenyl sulfate can be measured or quantitatively determined, and specific examples include mass spectrometry using a mass spectrometer (MS) and immunohistochemical staining, among which mass spectrometry is preferred.

Examples of the mass spectrometer (MS) include a liquid chromatograph mass spectrometer (LC/MS), a gas chromatograph mass spectrometer (GC/MS), a capillary electrophoresis-mass spectrometer (CE-MS), and an ELDI (Surface Enhanced Laser Desorption/Ionization) time-of-flight mass spectrometer (TOFMS).

An example of the immunohistochemical staining includes a method in which an antibody specifically bonding to a phenyl sulfate is used for performing analysis by latex agglutination immunoassay, fluorescent antibody technique, radioimmunoassay, immunoprecipitation, immune tissue staining, or Western blotting.

Now, the present invention will be more specifically described with reference to the Examples, and it is noted that the technical scope of the present invention is not limited to the following exemplified description.

Example 1

Plasma samples and urine samples were collected from 316 test subjects (including 143 males and 173 females) and the test subjects were tested for gender and eleven items (a phenyl sulfate salt [PS] concentration, a heart rate, a plasma glucose concentration, a hemoglobin A1c [HbA1c] value, a urine pH value, an estimated glomerular filtration rate [eGFR], a urinary albumin/creatinine ratio [ACR], a triglyceride [TG] level, a uric acid [UA] level, a blood urea nitrogen [BUN] level, and a pulse wave velocity [PWV] value). Multiple regression analysis was performed with the PS concentration used as a dependent function and with twelve values, that is, test values of the other ten items excluding the PS concentration and values corresponding to the age and the gender, used as independent variables. As a result, the PS concentration was more highly correlated with ACR corresponding to an index of early diabetic nephropathy than a plasma glucose concentration ($p=0.343$) and the HbA1c value ($p=0.351$) corresponding to indexes of diabetes, the eGFR ($p=0.512$) and the BUN level ($p=0.046$) corresponding to indexes of renal function, the TG level ($p=0.368$) corresponding to an index of liver function, the UA level ($p=0.524$) corresponding to an index of gout, or the PWV value ($0.213$) corresponding to an index of arteriosclerosis.

Joint Committee on Diabetic Nephropathy prescribed, in December 2013, a novel early diagnostic criterion that "a patient showing ACR of 30 to 299 mg/g is diagnosed with early diabetic nephropathy". Therefore, the test subjects were classified into groups respectively showing ACR of 0 to less than 30 (mg/g) (normal albuminuria), of 30 to 299 (mg/g) (microalbuminuria), and of not less than 300 (mg/g) (overt albuminuria) (respectively designated as a pre-nephropathy group, an early nephropathy group, and an overt nephropathy group), and the correlation with the PS concentration was checked (Table 1).

TABLE 1

| | ACR (mg/g) | | |
|---|---|---|---|
| | 0 to Less than 30 | 30 to 299 | Not less than 300 |
| | Number of Test Subjects | | |
| | 182 | 89 | 44 |
| Blood PS Concentration (nmol/mL) | 3.12 (0.41 to 54.4) | 4.88* (0.51 to 74.1) | 14.7** (1.42 to 159) |
| Urine PS concentration (nmol/mL) | 53.3 (3.47 to 843) | 40.1 (1.22 to 795) | 91.0*** (6.76 to 763) |
| eGFR (mL/min/1.73 m$^2$) | 68.9 ± 20.6 | 62.7 ± 23.6 | 38.8 ± 25.2 |

In this table, "*" indicates that there is a statistically significant difference ($p=0.035$) from a blood PS concentration (nmol/mL) of "ACR of 0 to less than 30 (mg/g)".

Besides, "**" indicates that there are statistically significant differences ($p=0.000192$ and $p=0.00111$ respectively) respectively from blood PS concentrations (nmol/mL) of "ACR of 0 to less than 30 (mg/g)" and "ACR of 30 to 300 (mg/g)".

Furthermore, "***" indicates that there are statistically significant differences ($p=0.000167$ and $p=0.00392$ respectively) respectively from urine PS concentrations (nmol/mL) of "ACR of 0 to less than 30 (mg/g)" and "ACR of 30 to 300 (mg/g)".

As a result, the blood PS concentration was higher in the early nephropathy group than in the pre-nephropathy group, and in the overt nephropathy group than in the early nephropathy group. This result reveals that the blood PS concentration increases as the stage of diabetic nephropathy defined based on a urinary albumin level proceeds (Table 1).

Besides, although there was no difference in the urine PS concentration between the pre-nephropathy group and the early nephropathy group, the urine PS concentration was higher in the overt nephropathy group than in the pre-nephropathy group and the early nephropathy group.

It was revealed, based on these results, that the stage (the early stage in particular) of diabetic nephropathy can be determined by using, as an index, the increase of the blood or urine PS concentration.

On the other hand, it is known that a blood PS concentration of a healthy individual is 0.07±0.02 (mg/dL) (≈4.0±1.1 [nmol/mL]) (document "Itoh, Y. et al., Anal. Bioanal. Chem. 2012, 403: 1841-1850"). In other words, assuming that the blood PS concentration derived from a healthy individual is normally distributed, healthy individuals showing a blood PS concentration of 4.0±1.1 (nmol/mL) occupy about 68% of the whole, healthy individuals showing a blood PS concentration of 4.0±2.2 (nmol/mL) occupy about 95% of the whole, and healthy individuals showing a blood PS concentration of 4.0±3.3 (nmol/mL) occupy about 99% of the whole. Therefore, the threshold value of the PS concentration was set to 5.5 (nmol/mL), 6.5 (nmol/mL) or 7.5 (nmol/mL) to check whether or not the PS concentration had increased before the onset of diabetic nephropathy (early nephropathy stage) (Table 2).

TABLE 2

| | ACR (mg/g) | | |
|---|---|---|---|
| | 0 to Less than 30 (Pre-nephropathy Stage) | 30 to 299 (Early Nephropathy Stage) | Not less than 300 (Overt Nephropathy Stage) |
| | Number of Test Subjects | | |
| | 182 | 89 | 44 |
| Less than 5.5 | 118 (65%) | 46 (52%) | 10 (23%) |
| Less than 6.5 | 125 (69%) | 54 (61%) | 12 (27%) |
| Less than 7.5 | 131 (72%) | 58 (65%) | 14 (32%) |
| Not less than 5.5 | 64 (35%) | 43 (48%) | 34 (77%) |
| Not less than 6.5 | 57 (31%) | 35 (39%) | 32 (73%) |
| Not less than 7.5 | 51 (28%) | 31 (35%) | 30 (68%) |

In this table, "Less than 5.5", "Less than 6.5", "Less than 7.5", "Not less than 5.5", "Not less than 6.5" and "Not less than 7.5" indicate blood PS concentrations (nmol/mL). Each parenthesized value (%) indicates a proportion in all the test subjects.

As a result, when the threshold values of the PS concentration was set to any of 5.5 (nmol/mL), 6.5 (nmol/mL) and 7.5 (nmol/mL), the PS concentration was increased in some test subjects in the pre-nephropathy stage before the onset of diabetic nephropathy (diabetic nephropathy at the early nephropathy stage) ("Not less than 5.5", "Not less than 6.5" and "Not less than 7.5" of Table 2).

Also in consideration of the results of Table 1 revealing that the stage of diabetic nephropathy can be determined by using the increase of the PS concentration as an index, it is presumed that a test subject showing the increase of the PS concentration before the onset of diabetic nephropathy has high risk of developing diabetic nephropathy. Besides, assuming that the blood PS concentration is normally distributed, the following can be said: In a test subject showing a blood PS concentration not less than 5.5 (nmol/mL), the blood PS concentration is higher than that of a healthy individual with at least a 84% probability, in a test subject showing a blood PS concentration not less than 6.5 (nmol/mL), the blood PS concentration is higher than that of a healthy individual with at least a 97.5% probability, and in a test subject showing a blood PS concentration not less than 7.5 (nmol/mL), the blood PS concentration is higher than that of a healthy individual with at least a 99.5% probability.

INDUSTRIAL APPLICABILITY

The present invention contributes to early detection and early treatment of diabetic nephropathy and prevention of onset of diabetic nephropathy.

The invention claimed is:

1. A method for preventing onset of diabetic nephropathy, comprising
    (a) collecting a biological sample from a test subject who has not developed diabetic nephropathy,
    (b) measuring a concentration of phenyl sulfate or salt thereof contained in the biological sample derived from the test subject;
    (c) diagnosing, when a concentration of the phenyl sulfate or salt thereof contained in the biological sample derived from the test subject is higher than a concentration of the phenyl sulfate or salt thereof contained in a biological sample derived from a healthy individual, that the test subject has a high possibility of developing diabetic nephropathy; and
    (d) administering an agent capable of onset of diabetic nephropathy to the diagnosed test subject.

2. The method for preventing onset of diabetic nephropathy according to claim 1, wherein the biological sample is blood or urine.

3. The method for preventing onset of diabetic nephropathy according to claim 2,
    wherein
    when a concentration of the phenyl sulfate or salt thereof contained in blood collected from the test subject is not less than a prescribed threshold value, it is indicative that the test subject has a high possibility of developing diabetic nephropathy.

4. The method for preventing onset of diabetic nephropathy according to claim 3, wherein the prescribed threshold value is 5.5 (nmol/mL).

* * * * *